US012788525B2

(12) United States Patent
Ledet et al.

(10) Patent No.: US 12,788,525 B2
(45) Date of Patent: *Nov. 10, 2026

(54) FORCE MEASURING APPARATUS

(71) Applicant: RENSSELAER POLYTECHNIC INSTITUTE, Troy, NY (US)

(72) Inventors: Eric Howard Ledet, Schenectady, NY (US); Sydney Marie Caparaso, Monroe, CT (US); Katerina Vladimirovna Kradinova, Boxborough, MA (US); Elizabeth Anne Capogna, Rexford, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 370 days.

This patent is subject to a terminal disclaimer.

(21) Appl. No.: 17/897,349

(22) Filed: Aug. 29, 2022

(65) Prior Publication Data

US 2023/0120005 A1 Apr. 20, 2023

Related U.S. Application Data

(63) Continuation of application No. 17/050,122, filed as application No. PCT/US2019/029094 on Apr. 25, 2019, now Pat. No. 11,426,250.

(60) Provisional application No. 62/662,649, filed on Apr. 25, 2018.

(51) Int. Cl.

| | |
|---|---|
| ***A61B 90/00*** | (2016.01) |
| ***A61B 17/64*** | (2006.01) |
| ***A61B 17/70*** | (2006.01) |
| ***A61B 17/80*** | (2006.01) |
| ***A61B 17/88*** | (2006.01) |

(52) U.S. Cl.

CPC .............. *A61B 90/06* (2016.02); *A61B 17/64* (2013.01); *A61B 17/7059* (2013.01); *A61B 17/80* (2013.01); *A61B 17/8869* (2013.01); *A61B 2090/064* (2016.02)

(58) Field of Classification Search

CPC ..... A61B 17/64; A61B 17/7059; A61B 17/80; A61B 17/8869; A61B 90/06; A61B 2090/064

See application file for complete search history.

(56) References Cited

U.S. PATENT DOCUMENTS

| | | | |
|---|---|---|---|
| 3,386,437 | A | 6/1968 | Treace |
| 5,797,912 | A | 8/1998 | Runciman et al. |
| 8,814,868 | B2 | 8/2014 | Janna et al. |
| 9,445,720 | B2 | 9/2016 | Janna et al. |
| 9,662,066 | B2 | 5/2017 | Ledet et al. |

(Continued)

OTHER PUBLICATIONS

International Search Report and The Written Opinion of the International Searching Authority, International Application No. PCT/US2019/029094, mailed Aug. 9, 2019.

*Primary Examiner* — Sameh R Boles

(74) *Attorney, Agent, or Firm* — Barclay Damon LLP; Anthony P. Gangemi

(57) ABSTRACT

A force measuring apparatus is described. The apparatus includes a force concentrator. The force concentrator is configured to attach to a loadbearing medical device and to produce a transverse force related to an eccentric axial force applied to the loadbearing medical device. A bending stiffness of the force concentrator is different from a bending stiffness of the loadbearing medical device.

8 Claims, 9 Drawing Sheets

(56) References Cited

U.S. PATENT DOCUMENTS

| | | | | |
|---|---|---|---|---|
| 10,010,429 | B2 | 7/2018 | Dmuschewsky | |
| 2004/0220571 | A1 | 11/2004 | Assaker et al. | |
| 2006/0052782 | A1 | 3/2006 | Morgan et al. | |
| 2006/0235407 | A1 * | 10/2006 | Wang | A61B 17/8071 606/281 |
| 2007/0173837 | A1 | 7/2007 | Chan et al. | |
| 2008/0161861 | A1 * | 7/2008 | Huebner | A61B 17/8085 606/286 |
| 2010/0106247 | A1 * | 4/2010 | Makower | A61B 17/8004 623/13.12 |
| 2016/0361070 | A1 | 12/2016 | Ardel et al. | |
| 2017/0360358 | A1 | 12/2017 | Amiot et al. | |
| 2018/0078201 | A1 | 3/2018 | Behzadi | |
| 2018/0228428 | A1 | 8/2018 | Anker et al. | |

* cited by examiner

FORCE MEASURING APPARATUS

CROSS REFERENCE TO RELATED APPLICATION(S)

This application is a continuation of and claims the benefit of U.S. Nonprovisional patent application Ser. No. 17/050,122, filed Oct. 23, 2020, that claims the benefit of International Patent Application number PCT/US2019/029094, filed Apr. 25, 2019, that claims the benefit of U.S. Provisional Application No. 62/662,649, filed Apr. 25, 2018, the entire disclosures of which are hereby incorporated by reference as if disclosed herein in their entireties.

GOVERNMENT LICENSE RIGHTS

This invention was made with government support under a Cooperative Technology Administration Agreement with the U.S. Department of Veterans Affairs. The government has certain rights in the invention.

FIELD

The present disclosure relates to a force measuring apparatus, in particular to, a force measuring apparatus for loadbearing medical devices.

BACKGROUND

A bone fracture may be stabilized with a cast worn over a period of time configured to allow new bone to form and the fracture to heal. Such a cast may not be sufficient for relatively more severe fractures. For the severe fracture case, a fracture plate, for example, may be surgically placed directly on the bone (e.g., outer surface of the bone) configured to span from above the fracture to below the fracture. The fracture plate may be attached to the bone by one or more fasteners, for example, screws. Thus, the fracture plate is placed in parallel with the damaged bone. As the bone is loaded, for example as a patient steps down and puts weight on a fractured leg, the load (i.e., force) may be split between the bone and the fracture plate.

The amount of force that is flowing through the bone versus the amount of force flowing through the fracture plate may be proportional to the stiffness of the bone relative to the stiffness of the fracture plate. Initially, when there has been a fracture, the bone may have approximately zero stiffness. In other words, no force will flow through the bone and all forces will flow through the fracture plate. As the bone starts to heal, the stiffness of the bone may very gradually increase and the proportion of force that is transmitted through the bone versus through the fracture plate may then change. As the bone continues to heal, a larger proportion of force may be transmitted through the bone. Thus, the amount of force experienced by the fracture plate over time may provide an indication of the status of the bone healing process.

SUMMARY

In some embodiments, an apparatus includes a force concentrator. The force concentrator is configured to attach to a loadbearing medical device and to produce a transverse force related to an eccentric axial force applied to the loadbearing medical device. A bending stiffness of the force concentrator is different from a bending stiffness of the loadbearing medical device.

In some embodiments of the apparatus, the force concentrator defines at least one aperture configured to align with an aperture defined in the loadbearing medical device and configured to receive a fastener. The fastener is configured to attach the force concentrator to the loadbearing medical device and to attach the loadbearing medical device to a bone structure.

In some embodiments of the apparatus, the force concentrator includes at least one attachment feature configured to engage with a corresponding attachment feature defined in the loadbearing medical device to attach the force concentrator to the loadbearing medical device.

In some embodiments of the apparatus, the force concentrator includes a sensor coupling feature configured to facilitate coupling the force concentrator to an axial force sensor attached to the loadbearing medical device.

In some embodiments of the apparatus, the force concentrator has an inner surface, an opposing outer surface and a side surface coupled between the inner surface and the outer surface. A portion of the inner surface is configured to contact an outer surface of the loadbearing medical device.

In some embodiments of the apparatus, the force concentrator includes at least one tensile member. In some embodiments of the apparatus, the force concentrator is constructed of a material selected from the group including metals, polymers and composite materials.

In some embodiments of the apparatus, a shape of the force concentrator is determined based, at least in part, on a target bending stiffness of the force concentrator.

In some embodiments, a system includes a loadbearing medical device, a force concentrator attached to the loadbearing medical device and an axial force sensor attached to the loadbearing medical device. The loadbearing medical device is configured to be attached to a bone structure. The force concentrator is configured to produce a transverse force related to an eccentric axial force applied to the loadbearing medical device. A bending stiffness of the force concentrator is different from a bending stiffness of the loadbearing medical device. The axial force sensor is configured to measure the transverse force.

In some embodiments of the system, the force concentrator defines at least one aperture configured to align with an aperture defined in the loadbearing medical device and configured to receive fastener. The fastener is configured to attach the force concentrator to the loadbearing medical device and to attach the loadbearing medical device to the bone structure.

In some embodiments of the system, the force concentrator includes at least one attachment feature configured to engage with a corresponding attachment feature defined in the loadbearing medical device to attach the force concentrator to the loadbearing medical device. In some embodiments of the system, the force concentrator includes a sensor coupling feature configured to facilitate coupling the force concentrator to the axial force sensor.

In some embodiments of the system, the force concentrator has an inner surface, an opposing outer surface and a side surface coupled between the inner surface and the outer surface. A portion of the inner surface is configured to contact an outer surface of the loadbearing medical device. In some embodiments of the system, the force concentrator includes at least one tensile member. In some embodiments of the system, the force concentrator is constructed of a material selected from the group including metals, polymers and composite materials.

In some embodiments of the system, a shape of the force concentrator is determined based, at least in part, on a target bending stiffness of the force concentrator. In some embodiments of the system, the fastener is selected from a group including screws, pins, wires, clips, clamps, retainers, bolts, rods, tethers and/or adhesives. In some embodiments of the system, the loadbearing medical device is selected from the group including a fracture plate, a spinal plate, a pedicle screw system or an external fixator. In some embodiments of the system, the loadbearing medical device is attached to a bone structure and the transverse force represents a healing condition of the bone structure. In some embodiments of the system, the force sensor is selected from the group including a load cell, a microelectromechanical (MEMS) force sensor, implantable force sensor and wireless force transducer.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Continuing with the leg example, when the person is stepping down on the leg, the forces that are running longitudinally along the length of the bone are generally applied to the center of the bone, i.e., axially. Since the fracture plate is positioned on an outside surface of the bone, the corresponding force on the fracture plate may not be centered axially on the fracture plate and is thus an eccentric axial force. The eccentric axial force applied to the fracture plate may then result in a bending moment in the fracture plate that may then cause the fracture plate to deform, i.e., bend.

Generally, a force measuring apparatus is described. A force measuring apparatus may include a force concentrator configured to attach to a loadbearing medical device. The loadbearing medical device may be configured to attach to a bone structure. As used herein, a bone structure may include, but is not limited to, a bone, a fractured bone, two adjacent vertebral bodies, etc. A bending stiffness of the force concentrator is different from a bending stiffness of the loadbearing medical device. When attached to the loadbearing medical device, the force concentrator is configured to produce a transverse force related to an eccentric axial force applied to the loadbearing medical device.

The eccentric axial force is related to an axial force applied to the bone to which the loadbearing medical device is attached. The transverse force may then be measured by an axial force sensor attached to the loadbearing medical device. The axial force sensor may be positioned transverse to the axial direction of the load applied to the loadbearing medical device and is configured to measure a transverse force between the loadbearing medical device and the force concentrator.

Figure 1:
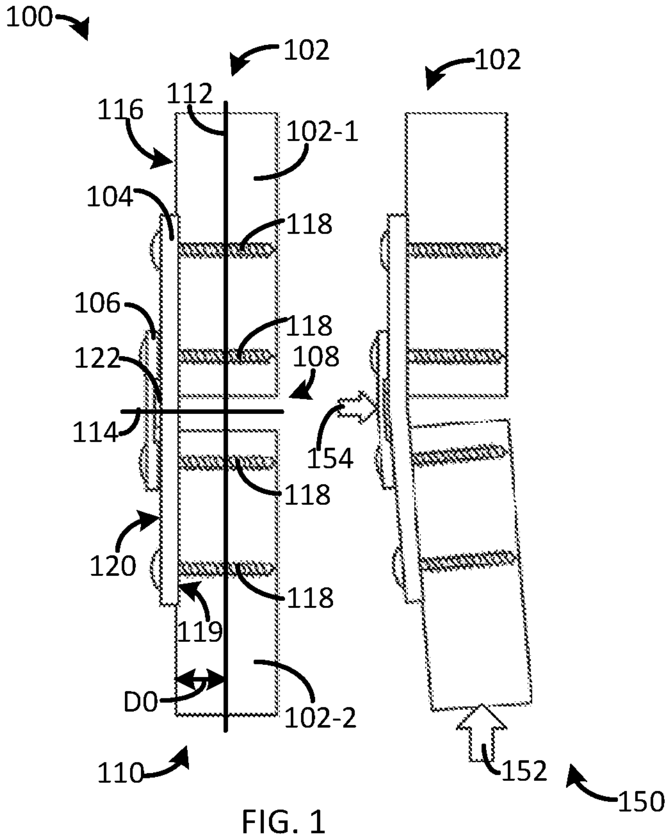
FIG. 1 is a sketch illustrating a fractured bone, a loadbearing medical device and a force concentrator, in an unloaded state and a loaded state.

FIG. 1 is a sketch 100 illustrating a fractured bone 102, a loadbearing medical device 104 and a force concentrator 106, in an unloaded state 110 and a loaded state 150. In this sketch, the loadbearing medical device 104 corresponds to a fracture plate. However, this disclosure is not limited in this regard. The fractured bone 102 has an upper portion 102-1 and a lower portion 102-2 separated by a gap 108 representing the fracture. A longitudinal axis 112 (e.g., a long axis of bone 102) is generally centered on the fractured bone 102. A transverse axis 114 is generally centered in the gap 108 and is perpendicular to the longitudinal axis 112.

The fractured bone 102 has an outer surface 116. The fracture plate 104 has an inside (inner) surface 119 and an outside (outer) surface 120. The fracture plate 104 is attached to the bone 102 by at least one fastener 118 so that at least a portion of the fracture plate 104 inner surface 119 contacts the bone outer surface 116. Fasteners may include, but are not limited to, screws, pins, wires, clips, clamps, retainers, bolts, rods, tethers, adhesives, etc. When attached to the bone 102, the inner surface 119 of the fracture plate 106 may be offset from the center axis 112 by distance D0.

The force concentrator 106 is attached to the fracture plate 104, positioned on the outer surface 120. The force concentrator 106 spans the gap 108. An axial force sensor 122 is positioned in or on the loadbearing medical device 104 and is configured to measure a transverse force, in a direction generally perpendicular to the longitudinal axis 112, i.e. generally perpendicular to the long axis of bone 102. The force sensor may include, but is not limited to, a load cell, a microelectromechanical (MEMS) force sensor, implantable force sensor, wireless force transducer, etc. When the fracture plate 104 is in a neutral state, e.g., when the bone 102 is not loaded, the axial force sensor may be configured to measure a neutral (minimum or zero) a transverse force.

It may be appreciated that the forces experienced by the fracture plate 104 and/or the force concentrator 106, in this example, may be tensile on an outside (i.e., outer) surface or may be tensile throughout the device. In other words, the loading is eccentric compression that may be a combination of bending and compression on the fracture plate 104 and force concentrator 106. If the ratio of compression is very high relative to the bending, the fracture plate 104 may be in compression rather than tension. If the ratio of bending is high relative to the compression, then the fracture plate 104 and the force concentrator 106 may both be in tension. It is contemplated that the inner surface 119 of the fracture plate 104 may be in compression and the outer surface 120 may be in tension.

In the loaded state 150, i.e., when a longitudinal, i.e., axial, force 152 is applied to the bone 102, an eccentric axial force may result in a bending moment in the loadbearing medical device 104. The bending moment may then deflect the loadbearing medical device 104 from its neutral position with respect to the longitudinal axis 112. The deflection of the loadbearing medical device 104 may then cause the axial force sensor 122 to contact and/or press on the force concentrator 106 resulting in a transverse force that may be measured by the axial force sensor 122. In one nonlimiting example, the transverse force may be proportional to the eccentric axial force. In another nonlimiting example, the transverse force may be nonlinearly related to the eccentric axial force.

A bending stiffness of the force concentrator 106 may be different from a bending stiffness of the loadbearing medical device 104. This difference in bending stiffness may result in a difference in radii of curvature between the loadbearing medical device 104 and the force concentrator 106. Such difference may then facilitate production of the transverse force 154 measured by the axial force sensor 122 and related to the eccentric axial force.

Figure 2:
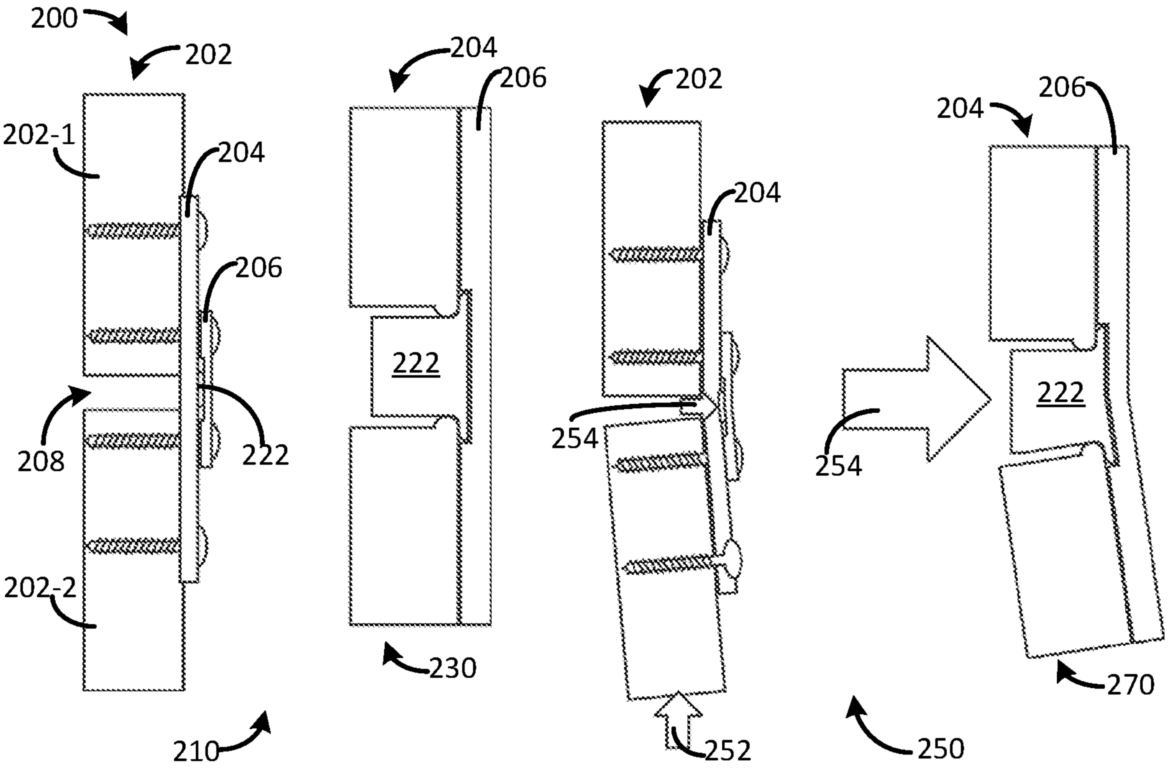
FIG. 2 is a sketch illustrating a fractured bone, a loadbearing medical device, and a force concentrator, in an unloaded state and a loaded state.

FIG. 2 is a sketch 200 illustrating a fractured bone 202, a loadbearing medical device 204, a force sensor 222 and a force concentrator 206, in an unloaded state 210 and a loaded state 250. It may be appreciated that the loadbearing medical device 204 and the force concentrator 206, in this example, are positioned on the compression side of the bone 202. The fractured bone 202 has an upper portion 202-1 and a lower portion 202-2 separated by a gap 208. In this sketch 200, when the loadbearing medical device 204 deflects in compression, the axial force sensor is configured to compress against the force concentrator 206.

Sketch 200 includes close-up cross-sections of the axial force sensor 222 and force concentrator 206 in an unloaded state 230 and in a loaded state 270. In this example, the axial force sensor 222 may be partially recessed in a feature in or on the loadbearing medical device configured to receive the axial force sensor. In one nonlimiting example, the axial force sensor 222 may be partially recessed in an existing screw hole defined in the loadbearing medical device 204. In another nonlimiting example, the axial force sensor 222 may be at least partially recessed in a feature in the loadbearing medical device 204 specifically configured to receive the axial force sensor.

In the loaded state 250, i.e., when an axial force 252 is applied to the bone 202, the loadbearing medical device 204 may experience a corresponding eccentric axial force and may deflect causing the axial force sensor 222 to contact and/or press on the force concentrator 206. The deflected loadbearing medical device 204 may then press the axial force sensor 222 up against the force concentrator 206. Pressing the axial force sensor 222 against the force concentrator 206 may then produce a transverse force 254 in the axial force sensor 222 proportional to the applied load.

Thus, a force concentrator and an axial force sensor may be attached to a loadbearing medical device. The force concentrator may be configured to produce a transverse force related to an eccentric axial force applied to the loadbearing medical device. The loadbearing member may be attached to a bone structure. The eccentric axial force may correspond to an axial force (i.e., load) on the bone structure. The transverse force may then be measured by an axial force sensor.

Figure 3:
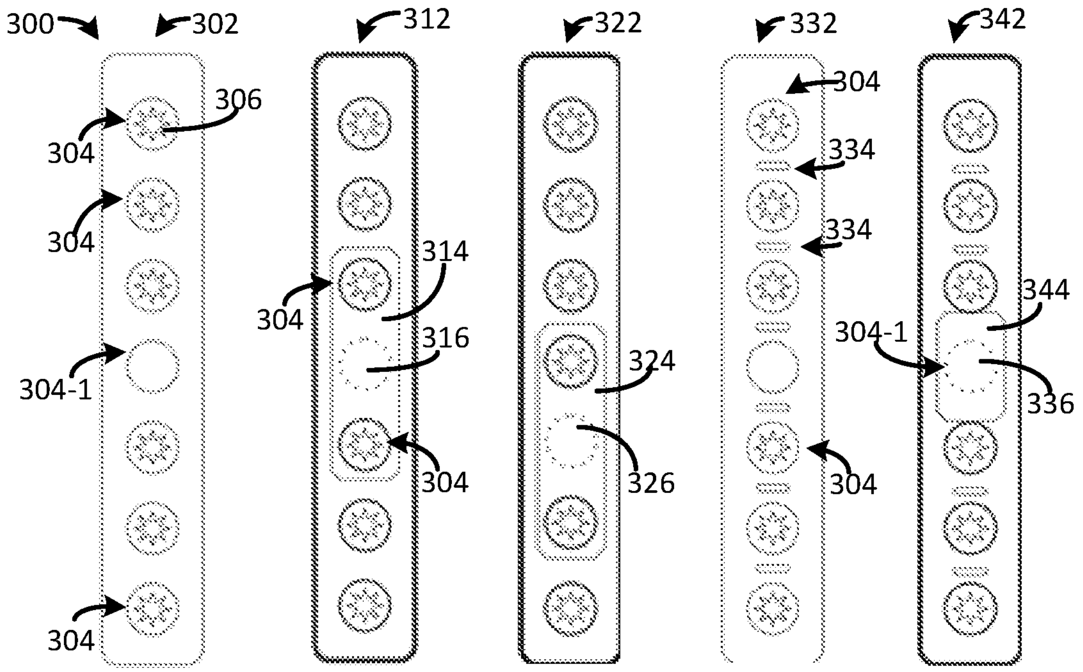
FIG. 3 illustrates outer surface views of a number of example fracture plates.

FIG. 3 illustrates outer surface (e.g., top) views 300 of a number of example fracture plates. Fracture plates (e.g., fracture plates 302, 312, 322, 332, 342) are one example of loadbearing medical devices. A first example fracture plate 302 is generally rectangular and defines a plurality of apertures, e.g., holes 304. This first example fracture plate 302 defines seven holes. However, this disclosure is not limited in this regard. Six of the holes 304 contain a head of a screw, e.g., screw 306. One hole 304-1 does not contain a screw. In an embodiment, hole 304-1 may be configured to contain a force sensor. Advantageously, positioning a force sensor in an existing hole in a fracture plate facilitates use of an off-the-shelf fracture plate in a force sensing apparatus, as described herein.

A second example fracture plate 312 corresponds to the first example fracture plate 302 with a force concentrator 314 mounted on an outer surface of the fracture plate 312 by two screws 306. In this example, the force concentrator 314 is centered on the fracture plate 312 and spans three screw holes. In this example 312, a force sensor 316 is positioned in the fracture plate 312 below the force concentrator 314 and the centered screw hole 304-1.

A third example fracture plate 322 illustrates a force concentrator 324 and axial force sensor 326 positioned asymmetrically on fracture plate 322. In other words, in the second example fracture plate 312, the force concentrator 314 and axial force sensor 316 were centered in a longitudinal direction on the fracture plate 312. In this third example, an end of the force concentrator 324 is positioned near a center of the fracture plate 322. For example, a screw mounted in aperture 304-1 may correspond to one of two attachment points configured to attach force concentrator 324 to the fracture plate 322.

A fourth example fracture plate 332 illustrates a plurality of attachment features 334 positioned between apertures 304. In this example 332, the attachment features 334 are slots with a generally rectangular shape and rounded corners. These attachment features 334 may be configured to receive an attachment feature, for example, a clip or a tab, of a force concentrator. In other words, in this example, a force concentrator may be attached to the fracture plate 332 via attachment features specifically designed for this purpose and thus without occupying existing mounting apertures.

A fifth example fracture plate 342 corresponds to fracture plate 332 with a force concentrator 344 mounted generally centered on the fracture plate 342. In this example 342, the force concentrator 344 may include attachment features configured to engage with the attachment features of the fracture plate 332 and a force sensor 336 may be positioned in a mounting hole 304-1.

Thus, the outer surface views 300 of FIG. 3 illustrate a number of embodiments of mounting and positioning a force concentrator on a fracture plate. The outer surface views 300 further illustrate positioning an axial force sensor in an aperture, e.g., a screw hole, defined in the fracture plate.

Figure 4:
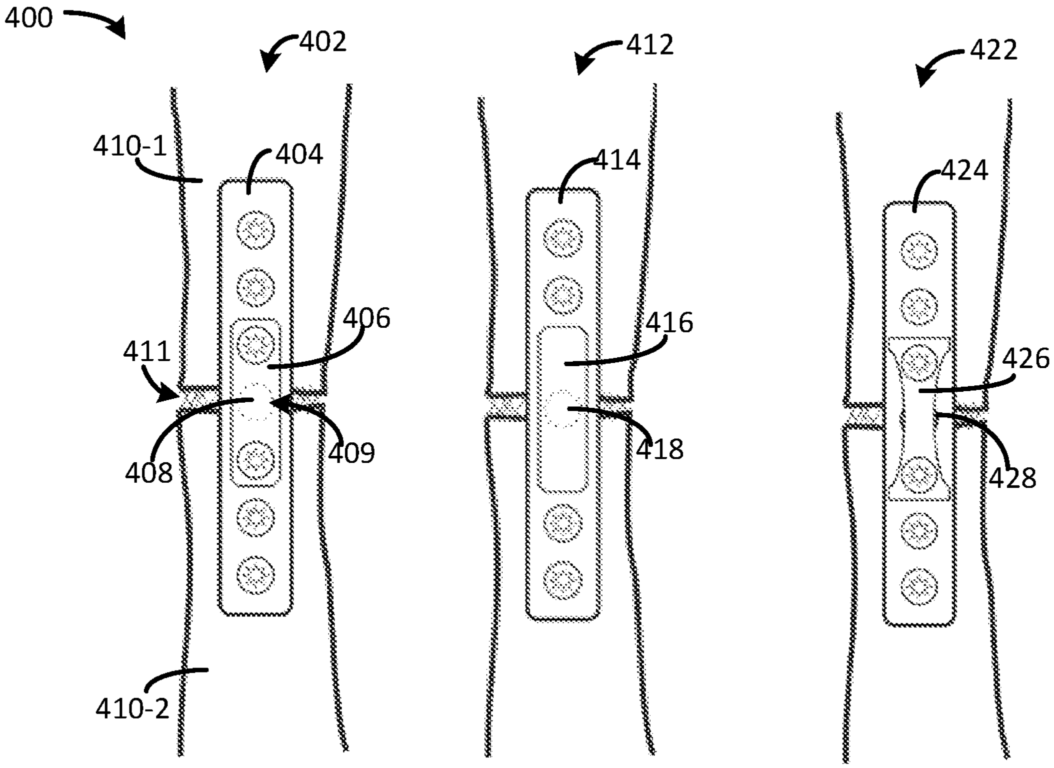
FIG. 4 illustrates outer views of example assemblies, including a fracture plate, a force concentrator and an axial force sensor, mounted on a fractured bone.

FIG. 4 illustrates outer views 400 of example assemblies, including a fracture plate, a force concentrator and an axial force sensor, mounted on a fractured bone. A first example 402 includes a fracture plate 404, a force concentrator 406 and an axial force sensor 408. The force concentrator 406 and axial force sensor 408 are attached to the fracture plate 404. At least the fracture plate 404 is attached to a top portion 410-1 and a bottom portion 410-2 of a fractured bone. The top portion 410-1 and the bottom portion 410-2 of the fractured bone are separated by a gap 411 corresponding to the fracture. The fracture plate 404 and the force concentrator 406 span the gap 411 between the upper portion 410-1 and the lower portion 410-2 of the fractured bone. In this example 402, the fracture plate 404 and the force concentrator 406 are generally rectangular and are attached to the bone via fasteners, i.e., screws, positioned in mounting holes in the fracture plate 404. A center mounting hole 409 is configured to contain the force sensor 408. The configuration of the fracture plate 404, force concentrator 406 and axial force sensor 408 of this first example 402 corresponds to the configuration of the second example 312 of FIG. 3.

A second example 412 illustrates a fracture plate 414. Example 412 further includes a force concentrator 416 and a force sensor 418 attached to the fracture plate 414. In this second example 412, the force concentrator 416 is attached to the fracture plate 414 by an attachment feature in the fracture plate 414 and a corresponding attachment feature in the force concentrator 416. In other words, in this second example, the attachment feature in the fracture plate 414 is specifically configured to engage the attachment feature of the force concentrator 416. Both the fracture plate 414 and the force concentrator 416 span the gap 418 corresponding to the fracture.

A third example 422 illustrates a fracture plate 424 and a force concentrator 426 and a force sensor 428 attached to the fracture plate 424. In this third example 422, the force concentrator 426 has a shape configured to reduce a bending stiffness of the force concentrator 426 relative to a bending stiffness of the fracture plate 424. In this third example 422, the force concentrator 426 is configured to taper resulting in a relatively smaller cross-section at or near the force sensor 428. It may be appreciated that reducing the bending stiffness of the force concentrator 426 via geometry may facilitate using similar or same materials for the fracture plate 424 and the force concentrator 426 while maintaining a bending stiffness difference between the fracture plate 424 and the force concentrator 426.

Figure 5:
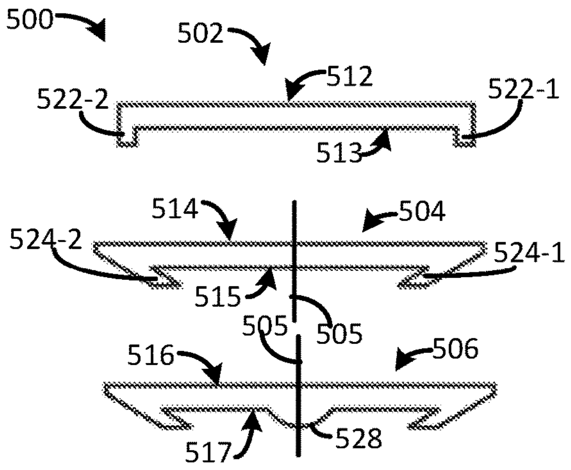
FIG. 5 illustrates side views of examples of force concentrators illustrating example attachment features and an example force sensor coupling feature.

Thus, outside surface views 400 illustrate a variety of force concentrator configurations and attachment techniques for attaching the force concentrator to the loadbearing medical device. FIG. 5 illustrates side views 500 of examples of force concentrators illustrating example attachment features and an example force sensor coupling feature. In all three examples, the attachment features are positioned at opposing ends of the force concentrator. However, this disclosure is not limited in this regard. A first example force concentrator 502 has a top (i.e., outer) surface 512 and an opposing bottom (i.e., inner) surface 513. The first example force concentrator 502 includes a first attachment feature 522-1 and a second attachment feature 522-2. Each attachment feature 522-1, 522-2 is configured to engage with a respective corresponding attachment feature included in a loadbearing medical device. For example, the corresponding attachment features in the loadbearing medical device may be apertures defined in at least an outer surface of the loadbearing medical device. The attachment features 522-1, 522-2 may be configured to engage with (e.g., fit into) the corresponding apertures in the loadbearing medical device when the force concentrator 502 is attached to the loadbearing medical device. At least a portion of the inner surface 513 may be configured to contact the outer surface of the loadbearing medical device. In this example, the attachment features 522-1, 522-2 have a generally rectangular cross-section and project generally perpendicular from the inner surface 513.

A second example force concentrator 504 has a top (i.e., outer) surface 514 and opposing bottom (i.e., inner) surface 515. The second example force concentrator 504 includes a first attachment feature 524-1 and a second attachment feature 524-2. Each attachment feature 524-1, 524-2 is configured to engage with a respective corresponding attachment feature included in a loadbearing medical device. For example, the corresponding attachment features in the loadbearing medical device may be apertures defined in at least an outer surface of the loadbearing medical device. The attachment features 524-1, 524-2 may be configured to engage with (e.g., fit into) the corresponding apertures in the loadbearing medical device when the force concentrator 504 is attached to (i.e., engaged with) the loadbearing medical device. At least a portion of the inner surface 515 may be configured to contact the outer surface of the loadbearing medical device. In this example, the attachment features 524-1, 524-2 are generally symmetric and project at an angle of less than 90° towards a centerline 505 of the force concentrator 504. Thus, the attachment features 524-1, 524-2 may generally “clip” into the outer surface of the loadbearing medical device.

A third example force concentrator 506 is similar to the second force concentrator 504, has a top (i.e., outer) surface 516 and opposing bottom (i.e., inner) surface 517 and includes similar attachment features configured to engage with corresponding apertures in the loadbearing medical device when the force concentrator 506 is attached to (i.e., engaged with) the loadbearing medical device. At least a portion of the inner surface 517 may be configured to contact the outer surface of the loadbearing medical device.

This third example force concentrator 506 further includes a sensor coupling feature 528. The sensor coupling feature 528 may be positioned on and/or included in the inner surface 517 of the force concentrator 506. In an embodiment, the sensor coupling feature 528 may be generally centered at the centerline 505 of the force concentrator 506. The sensor coupling feature 528 is configured to facilitate contact between a force sensor attached to the loadbearing medical device and the force concentrator 506. A shape of the sensor coupling feature 528 may be generally curved as shown. However, this disclosure is not limited in this regard. The sensor coupling feature 528 may be configured to focus and/or concentrate the transverse axial force onto a force sensor positioned adjacent the inner surface of the force concentrator. The sensor coupling feature 528 may be configured to accommodate variation in force sensor geometries. In other words, a presence, a shape and/or a location of the sensor coupling feature 528 may be determined based, at least in part, on a selected axial force sensor.

Thus, side views 500 illustrate a variety of force concentrator attachment features for attaching a force concentrator to a loadbearing medical device.

Figure 6:
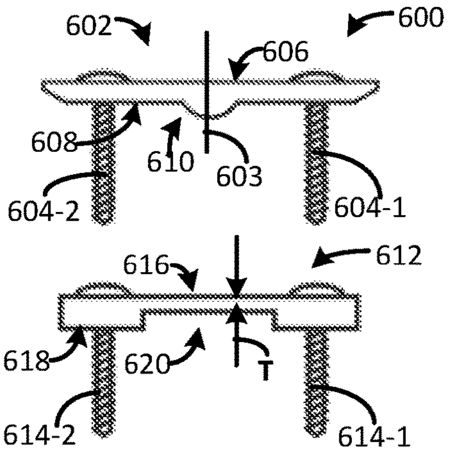
FIG. 6 illustrates side views of examples of force concentrators illustrating example force sensor coupling features.

FIG. 6 illustrates side views 600 of examples of force concentrators illustrating example force sensor coupling features. A first example force concentrator 602 has a top (i.e., outer) surface 606 and an opposing bottom (i.e., inner) surface 608. The first example force concentrator 602 is configured to be attached to a bone through corresponding apertures in a loadbearing medical device via fasteners (e.g., screws) 604-1, 604-2. The screws 604-1, 604-2 are positioned near opposing ends of the force concentrator 602 and are configured to extend through corresponding apertures defined in the first example force concentrator 602. First example force concentrator 606 may further include a sensor coupling feature 610 that is generally positioned near a centerline 603 of the example force concentrator 602 on the inner surface 608. In this example 602, the sensor coupling feature is generally curved. However, this disclosure is not limited in this regard.

A second example force concentrator 612 may similarly be attached to a bone structure through corresponding apertures in the loadbearing medical device via fasteners 614-1, 614-2 positioned near opposing ends of the second example force concentrator 612. Example force concentrator 612 has an outer surface 616 and an opposing inner surface 618. The force concentrator 612 has a feature 620 defined in the inner surface 618. A thickness, T, of the force concentrator 612 is less in the feature 620 region than regions closer to the fasteners 614-1, 614-2. In one embodiment, feature 620 may correspond to a sensor coupling feature that is configured to accommodate an axial force sensor, as described herein. In another embodiment, feature 620 and the associated lesser thickness, T, may be configured to reduce a bending stiffness of the force concentrator 612, for example, relative to a bending stiffness of a loadbearing medical device to which force concentrator 612 may be attached.

Thus, side views 600 illustrate to example force concentrator geometries and at least one sensor coupling feature.

Figure 7:
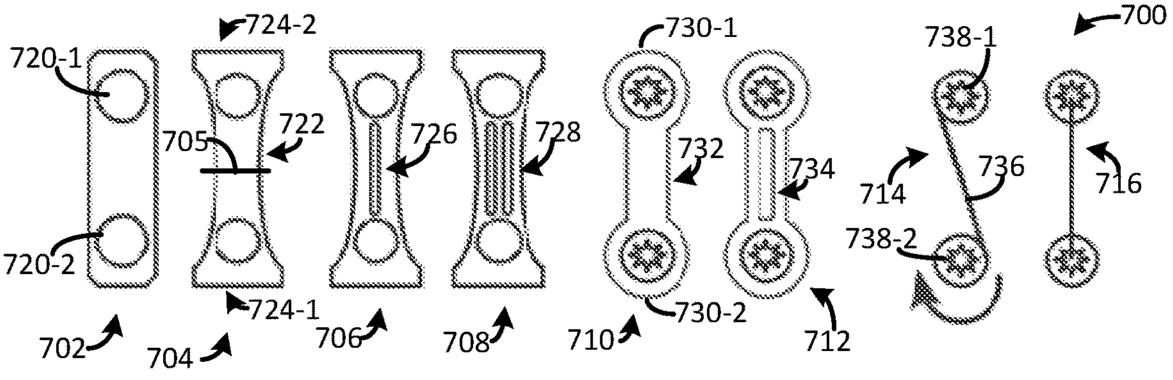
FIG. 7 illustrates outer views of example force concentrators illustrating a variety of geometries and a variety of bending stiffness characteristics.

FIG. 7 illustrates outer views 700 of example force concentrators illustrating a variety of geometries and a variety of bending stiffness characteristics. A force concentrator may be constructed of a variety of materials including, but not limited to, metals (e.g., titanium, titanium alloys, stainless steel, stainless steel alloys, etc.), polymers (e.g., polyethylene, polyetheretherketone (PEEK), polyurethane, polymethyl methacrylate, etc.) and/or composite materials (e.g., a carbon fiber reinforced polymer, etc.).

A first example force concentrator 702 has a generally rectangular shape and defines two apertures 720-1, 720-2 at opposing ends of the force concentrator 702 configured to receive corresponding fasteners. In one embodiment, the apertures may be generally circular. In another embodiment, one aperture may be elongated. The elongated aperture may, in some circumstances, allow one end of the force concentrator to move relative to the loadbearing medical device.

A second example force concentrator 704 has similar apertures as force concentrator 702. The second example force concentrator 704 has a relatively narrower center region 722 compared to the first example force concentrator 702. The second example force concentrator 704 illustrates a taper along the sides of the force concentrator 704 from the ends 724-1, 724-2 towards the center 705. The taper of the sides is configured to also taper (i.e., reduce) a cross section. A shape of the second example force concentrator 704 may be determined based, at least in part, on a target bending stiffness of the force concentrator 704. It may be appreciated that the relatively larger width near the ends 724-1, 724-2 relative to the center 705 may be configured to accommodate fasteners.

A third example force concentrator 706 has a shape similar to the second example force concentrator 704 and apertures configured to receive fasteners. The third example force concentrator 706 includes a feature 726 generally centered longitudinally between the apertures. In one embodiment, the feature 726 may be an aperture configured to reduce a bending stiffness of the force concentrator 706. In another embodiment, the feature 726 may be a structure configured to increase a bending stiffness of the force concentrator 706. A fourth example force concentrator 708 has a shape similar to the second and third example force concentrators 704, 706. The fourth example force concentrator 708 includes a plurality of features 728 similar to feature 726. In other words, features 728 may correspond to apertures configured to decrease a bending stiffness of the force concentrator 708 or a structure configured to increase the bending stiffness of the force concentrator 708.

A fifth example force concentrator 710 and a sixth example force concentrator 712 may each include eyelet features 730-1, 730-2 positioned at opposing ends of the respective force concentrator 710, 712. The eyelet features 730-1, 730-2 are configured to accommodate fasteners, e.g., screws. A portion 732 of the force concentrators between the eyelet features 730-1, 730-2 is configured to have a uniform width that is less than a diameter of the eyelets 730-1, 730-2. The width of the portion 732 may be related to a target bending stiffness of the force concentrator 710, 712. Similar to the third example force concentrator 706, force concentrator 712 may include a feature 734. The feature 734 may correspond to an aperture configured to reduce a bending stiffness of the force concentrator 712 or a structure configured to increase the bending stiffness of the force concentrator 712.

A seventh example force concentrator 714 and an eighth example force concentrator 716 may each include a tensile member, for example, a tether like material (e.g., a suture) 736. The tensile member 736 may span a region between two fasteners 738-1 738-2 configured to attach the tensile member 736 to a bone structure, as described herein. It may be appreciated that tensile member 736 may have a generally lesser bending stiffness compared to other example force concentrators, as described herein. In one nonlimiting example, the bending stiffness of the tensile member 736 may be adjusted by wrapping a portion of the tether around a screw, e.g., screw 738-2, and turning the screw (i.e., tightening or loosening) to increase or decrease the tension on the tensile member 736.

Thus, top views 700 illustrate a variety of force concentrator geometries that may be related to a relative bending stiffness of each respective force concentrator.

Figure 8:
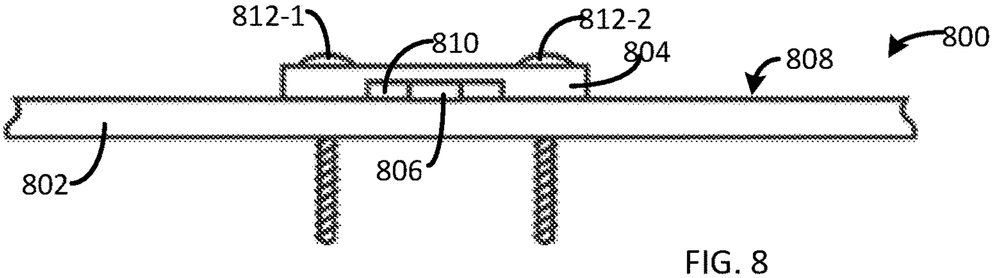
FIG. 8 illustrates one example assembly that includes a portion of a loadbearing medical device, a force concentrator and a force sensor.

FIG. 8 illustrates one example assembly 800 that includes a portion of a loadbearing medical device 802, a force concentrator 804 and a force sensor 806. In this example 800, the force concentrator 804 includes a feature (i.e., an opening) similar to force concentrator 612 of FIG. 6. The force sensor 806 may then extend above an outer surface 808 of the loadbearing medical device 802. The force sensor 806 may thus extend into an aperture 810 defined in an inner surface of the force concentrator 804. The aperture 810 may then correspond to a sensor coupling feature, as described herein. Example assembly 800 further includes two fasteners 812-1, 812-2 configured to attach the assembly to a bone structure. Thus, example assembly 800 may be mounted to a bone structure and configured to measure a transverse force produced as a result of an eccentric axial force on the bone structure.

Figure 9:
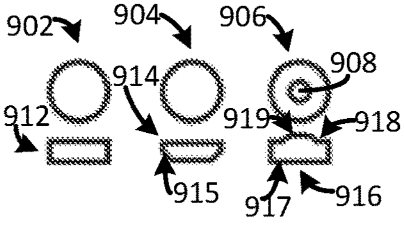
FIG. 9 illustrates a top view and a side view of three force sensor geometries.

FIG. 9 illustrates a top view and a side view of three force sensor geometries. However, this disclosure is not limited in this regard. Force sensor geometries may include, but are not limited to, circular, ellipsoidal, oblong, rectangular, trapezoidal, rectangular with rounded corners, trapezoidal with rounded corners, tapered, not tapered, etc. A top view of a first example force sensor 902 is generally circular and a corresponding side view 912 is generally rectangular. A top view of a second example force sensor 904 is also generally circular and a corresponding side view 914 is generally trapezoidal with tapers, e.g., taper 915, at opposing ends. A top view of a third example force sensor 906 is generally circular with a concentric center region 908. A side view of the third example for sensor 916 has a relatively flat bottom surface 917 and a top surface 918 with a raised center region 919. The raised center region 919 corresponds to the concentric center region 908 illustrated in the top view 906. Thus, a variety of force sensors and a corresponding variety of force sensor geometries may be utilized for the axial force sensor in a force measuring apparatus, as described herein.

Figure 10:
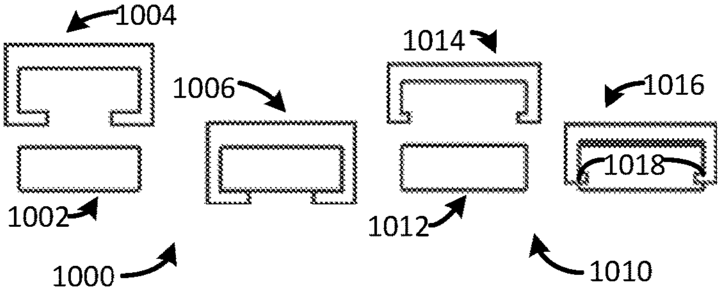
FIG. 10 illustrates end views of a loadbearing medical device (e.g., a fracture plate) and a force concentrator attachment feature for two embodiments of a force concentrator attachment feature.

FIG. 10 illustrates end views of a loadbearing medical device (e.g., a fracture plate) and a force concentrator attachment feature for two embodiments of a force concentrator attachment feature. A first example 1000 attachment feature includes an end view of a loadbearing medical device, e.g., a fracture plate 1002, and an end view 1004 illustrating a first force concentrator geometry. In this first example 1000, the force concentrator 1004 is configured to clip on the fracture plate 1002 as illustrated by assembly 1006. A second example 1010 attachment feature includes an end view of a loadbearing medical device, e.g., a fracture plate 1012, and an end view 1014 illustrating a second force concentrator geometry. In this second example 1010, the force concentrator 1014 is configured to clip on the fracture plate 1012 as illustrated by assembly 1016. In this example, the fracture plate may include a feature, e.g., may define a groove 1018, configured to engage an attachment feature. The groove 1018 may be configured to engage the force concentrator attachment feature. Thus, in these examples 1000, 1010, a force concentrator may be configured to clip on to a loadbearing medical device. However, this disclosure is not limited in this regard.

Figure 11:
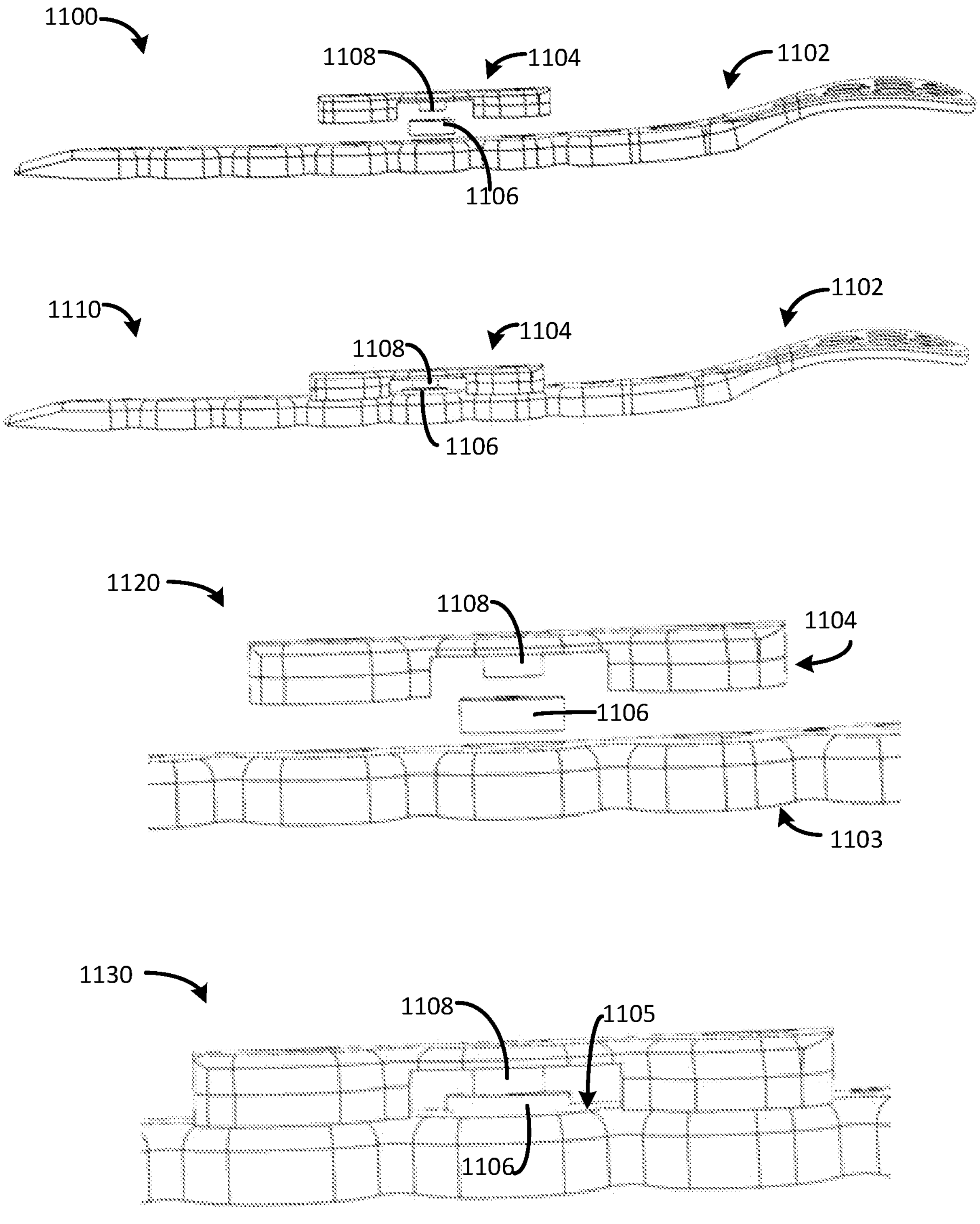
FIG. 11 illustrates side views including exploded and assembly views a loadbearing medical device, a force concentrator and a force sensor.

FIG. 11 illustrates side views including exploded and assembly views of a loadbearing medical device, a force concentrator and a force sensor. A first exploded view 1100 includes a loadbearing medical device 1102, a force concentrator 1104 and the force sensor 1106. In this example 1100, the force concentrator 1104 further includes a sensor coupling feature 1108. In this example 1100, the sensor coupling feature 1108 may be generally cylindrically shaped. However, this disclosure is not limited in this regard. Side view 1110 corresponds to the assembly of the first exploded view 1100. Side view 1110 illustrates the sensor coupling feature close to or contacting the force sensor.

A second exploded view 1120 includes the force concentrator 1104, a portion of the loadbearing medical device 1103, the force sensor 1106, and the sensor coupling feature 1108. Side view 1130 corresponds to the assembly of the second exploded view 1120. Side view 1130 illustrates the force sensor 1106 protruding above an outer surface 1105 of the loadbearing medical device. Side view 1130 further illustrates the sensor coupling feature 1108 contacting the force sensor 1106.

Figure 12:
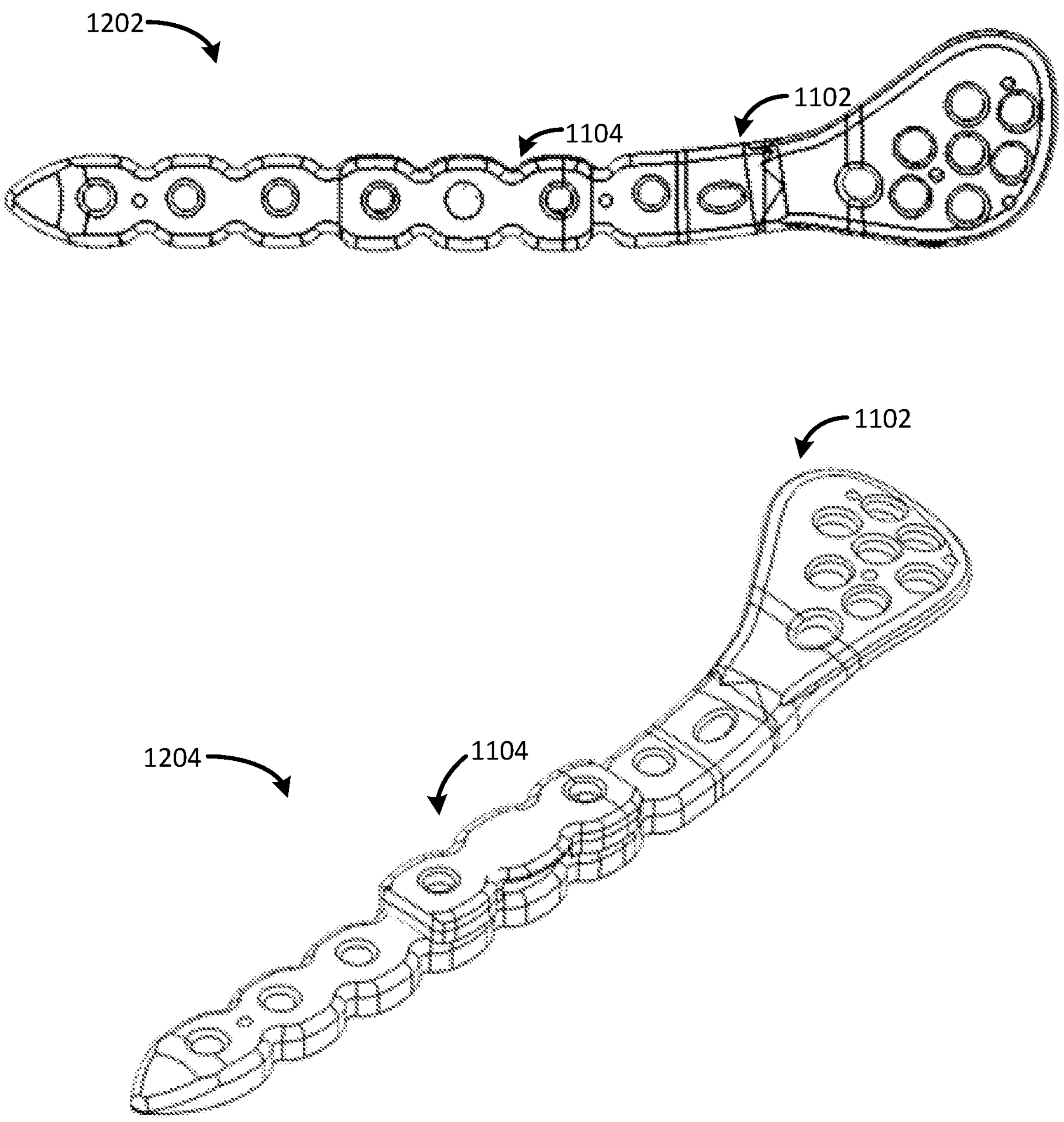
FIG. 12 illustrates a top view and an isometric view of the assembly of FIG. 11.

FIG. 12 illustrates a top view 1202 and an isometric view 1204 of the assembly of FIG. 11. The top view 1202 illustrates the loadbearing medical device, e.g., a fracture plate, 1102 with the load concentrator 1104 attached. The isometric view 1204 illustrates the fracture plate 1102 and the load concentrator 1104 attached.

Thus, a load concentrator and force sensor may be attached to a fracture plate.

Figure 13:
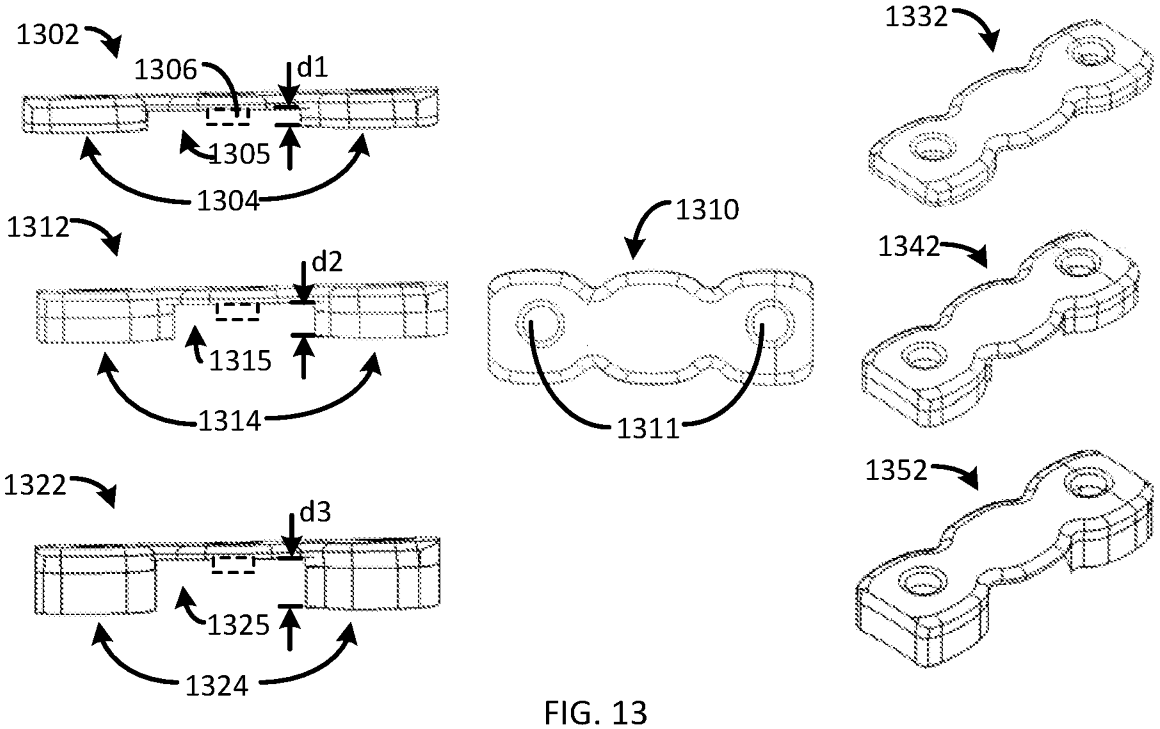
FIG. 13 illustrates side views, a top view and isometric views of a variety of force concentrators with a plurality of sensor coupling features.

FIG. 13 illustrates side views, a top view and isometric views of a variety of force concentrators with a plurality of sensor coupling features. A side view of a first force concentrator 1302 includes offsets 1304 at opposing ends of the force concentrator 1302. The offsets 1304 define an opening 1305 in a bottom surface of the force concentrator having depth d1. The opening 1305 and/or the offsets 1304 may then correspond to a sensor coupling feature, as described herein.

In some embodiments, the first force concentrator 1302 may include a second sensor coupling feature 1306. The second sensor coupling feature 1306 may be cylindrical and/or curve shaped. However, this disclosure is not limited in this regard. The second sensor coupling feature 1306 may be configured to focus forces onto a corresponding force sensor that may be positioned immediately below the force concentrator (i.e., between the force concentrator and the loadbearing medical device). In some embodiments, the first force concentrator 1302 may not include the second sensor coupling feature 1306.

A side view of a second force concentrator 1312 includes offsets 1314 at opposing ends of the force concentrator 1312 configured to define an opening 1315 having depth d2. A side view of a third force concentrator 1322 includes offsets 1324 at opposing ends of the force concentrator 1322 configured to define an opening 1325 having depth d3.

A top view 1310 consistent with any one or more of force concentrators 1302, 1312, 1322 includes openings 1311 positioned at opposing ends configured to receive respective fasteners, as described herein. Isometric view 1332 corresponds to force concentrator 1302; isometric view 1342 corresponds to force concentrator 1312 and isometric view 1352 corresponds to force concentrator 1322.

It may be appreciated, in comparing the first force concentrator 1302, the second force concentrator 1312 and the third force concentrator 1322, that $d1<d2<d3$. Thus, a sensor coupling feature, e.g., sensor coupling features 1305, 1315, 1325, may be configured to accommodate a variety of axial force sensors that may protrude above an outer surface of a corresponding loadbearing medical device.

Figure 14:
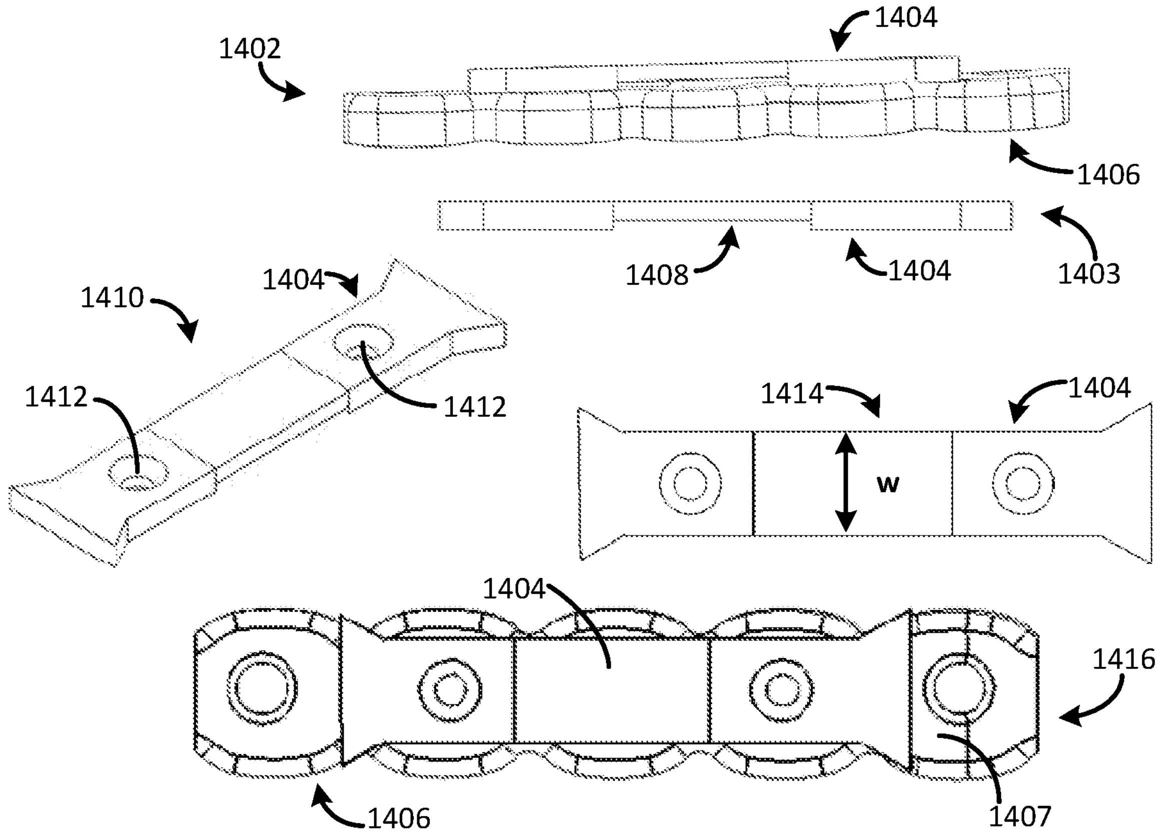
FIG. 14 illustrates a variety of views of another example force concentrator.

FIG. 14 illustrates a variety of views of another example force concentrator. A first side view 1402 includes a force concentrator 1404 attached to a loadbearing medical device 1406. A second side view 1403 illustrates an opening 1408 defined by the force concentrator 1404. The opening 1408 may be configured to accommodate a force sensor and/or to reduce a thickness of the force concentrator to achieve a target bending stiffness of the force concentrator 1404, as described herein. An isometric view 1410 of the force concentrator 1404 illustrates openings 1412 defined in the force concentrator 1404 configured to receive fasteners, as described herein. A top view 1414 of the force concentrator 1404 illustrates a width, w, of the force concentrator 1404. A top view 1416 illustrates the force concentrator 1404 mounted on an outer surface 1407 of the loadbearing medical device 1406. Thus, a geometry of a force concentrator may be configured to fit a geometry of a loadbearing medical device, accommodate a load sensor and/or achieve a target bending stiffness of the force concentrator.

Figure 15:
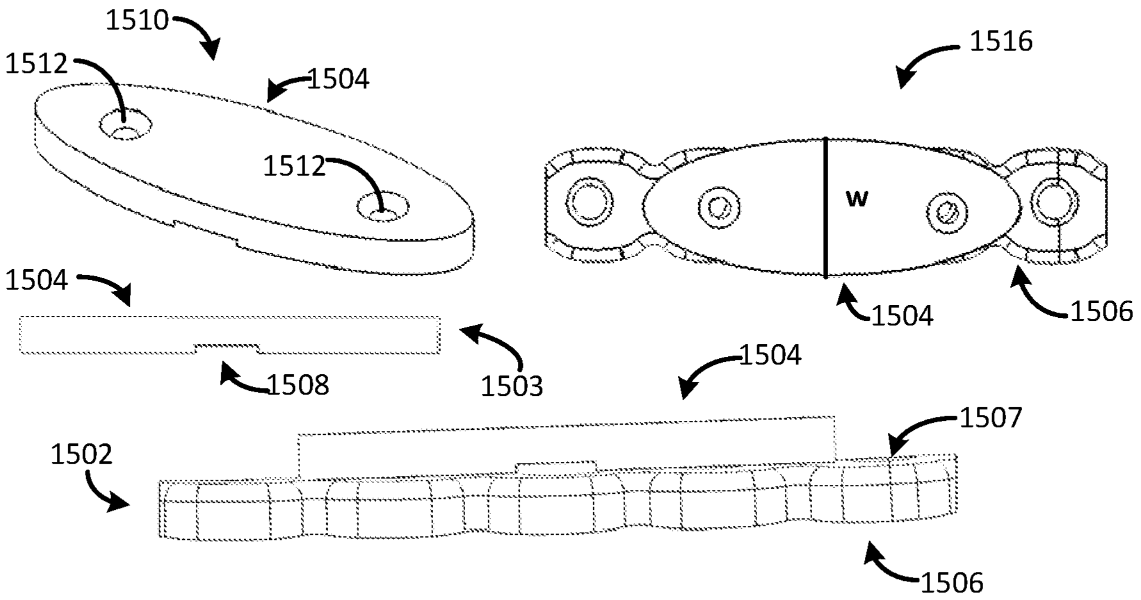
FIG. 15 illustrates a variety of views of another example force concentrator.

FIG. 15 illustrates a variety of views of another example force concentrator. A first side view 1502 includes a force concentrator 1504 attached to an outer surface 1507 of a loadbearing medical device 1506. A second side view 1503 illustrates an opening 1508 defined by the force concentrator 1504. The opening 1508 may be configured to accommodate a force sensor and/or achieve a target bending stiffness of the force concentrator 1504, as described herein. An isometric view 1510 of the force concentrator 1504 illustrates openings 1512 defined in the force concentrator 1504 configured to receive fasteners, as described herein. A top view 1516 illustrates the force concentrator 1504 attached to the loadbearing medical device 1506. The top view 1516 of the force concentrator 1404 illustrates variation in the width, w, of the force concentrator 1404 over its length. In this example, the force concentrator is generally ellipsoidal in shape. Thus, a geometry of a force concentrator may be configured to fit a geometry of a loadbearing medical device, accommodate a load sensor and/or affect a target bending stiffness of the force concentrator.

Figure 16:
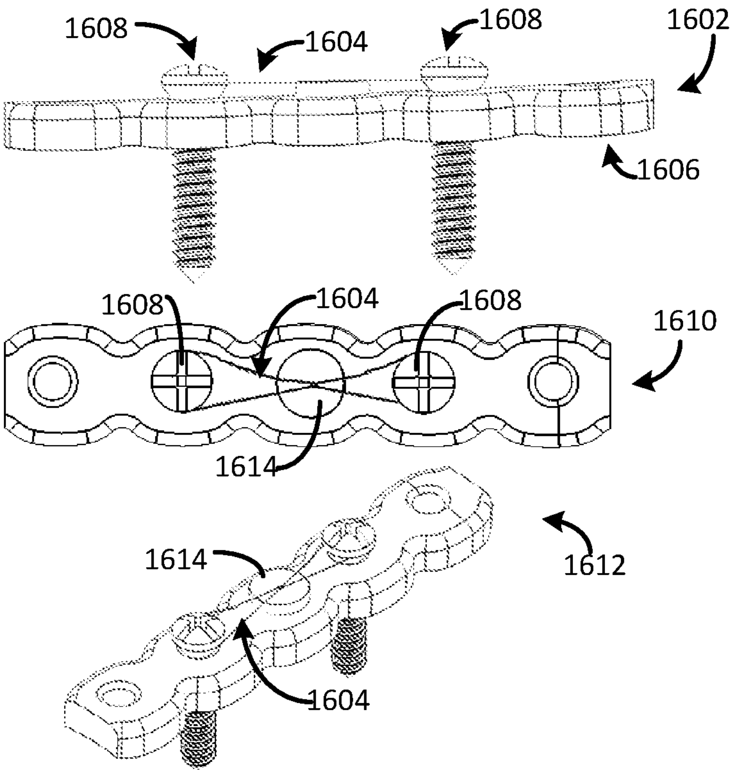
FIG. 16 illustrates a side view, a top view and an isometric view of an assembly including another example force concentrator.

FIG. 16 illustrates a side view 1602, a top view 1610 and an isometric view 1612 of an assembly including another example force concentrator. The assembly includes a force concentrator 1604, a loadbearing medical device, e.g., a fracture plate 1606 and a plurality of fasteners, e.g., screws 1608. In this example, the force concentrator 1604 is a tensile member including, but not limited to, a tether, a suture, etc. The tensile member 1604 is configured to cross at or near a force sensor 1614. In some embodiments, one or more of the screws 1608 may be tightened or loosened to adjust a tension in the tensile member 1604. In this example, the tension may be related to effective bending stiffness of the force concentrator.

Figure 17:
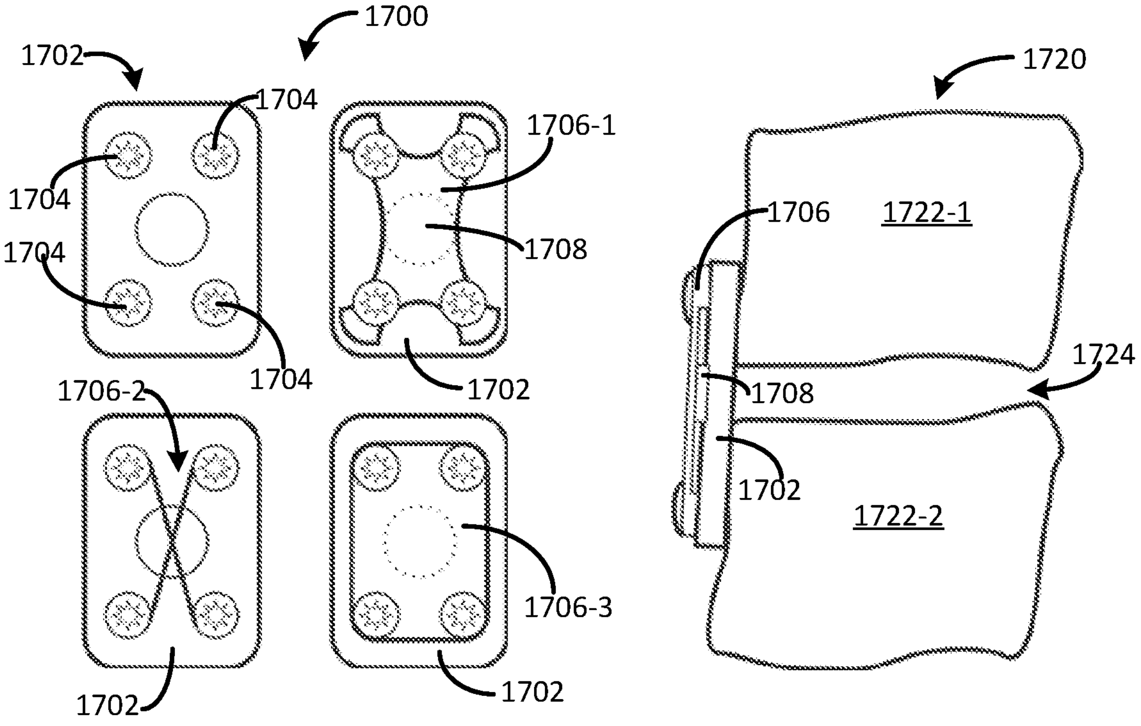
FIG. 17 illustrates a spinal plate example application of a force measuring apparatus, consistent with the present disclosure.

FIG. 17 illustrates a spinal plate example application of a force measuring apparatus, consistent with the present disclosure. FIG. 17 illustrates outer views 1700 of spinal plates, a force concentrator and an axial force sensor and a side view 1720 of a corresponding assembly mounted to two adjacent vertebral bones. In this spinal plate example, a force concentrator may be utilized with a spine plate 1702 configured to be coupled to the vertebral bodies by a plurality of fasteners 1704, as described herein. The example force concentrators may be coupled to the spine plate 1702 and/or the vertebral bodies by fasteners 1704. In one embodiment, an example force concentrator 1706-1 may have tapered sides and may be attached to the spine plate 1702 (and/or vertebral bodies) at or near the corners. In another embodiment, an example force concentrator 1706-2 may include one or more tensile members configured to be attached to the spine plate 1702 by screws 1704. In another embodiment, an example force concentrator 1706-3 may be generally rectangular shaped with rounded corners. Example force concentrator 1706-3 may be similarly attached to the spine plate 1702 by screws 1704.

A side view 1720 includes a plurality of vertebral bodies 1722-1, 1722-2 separated by a gap 1724. The gap 1724 may generally contain a spacer implant or a bone graft. The side view 1720 includes the spine plate 1702 attached to the vertebral bodies 1722-1, 1722-2 and spanning the gap 1724. A force concentrator 1706 is attached to an outer surface of the spine plate 1702 and a force sensor 1708 is attached spine plate 1702 configured to contact force concentrator 1706. For example, movement of the vertebral bodies relative to each other may deflect the spine plate 1702 resulting in a transverse axial force between the spine plate 1702 and the force concentrator 1706 that may then be measured by the force sensor 1708.

Thus, a force concentrator consistent with the present disclosure may be utilized with a loadbearing medical device such as a spine plate.

Figure 18:
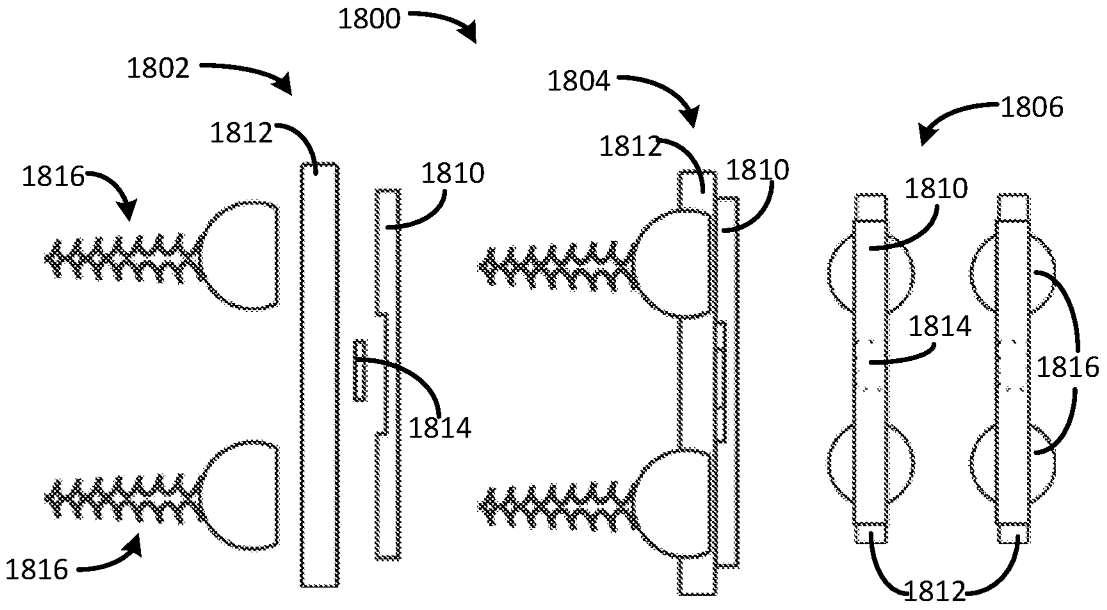
FIG. 18 illustrates a pedicle screw example application of a force measuring apparatus consistent with the present disclosure.

FIG. 18 illustrates a pedicle screw example application of a force measuring apparatus consistent with the present disclosure. In this example 1800, the force concentrator may be utilized in a pedicle screw system. Example 1800 includes a exploded side view 1802, an assembled side view 1804 and a top (i.e., outer, outside) view 1806 of two parallel pedicle screw systems. Example 1800 includes a force concentrator 1810, a pedicle rod 1812 (an example of a loadbearing medical device), a force sensor 1814 and a plurality of pedicle screws 1816. The pedicle screw system is similar to a fracture plate but may be utilized for the posterior spine. Force concentrator 1810 and the force sensor 1814 may be attached to the pedicle rod 1812. The pedicle rod 1812 may then be attached to the pedicle screws 1816. Deflection of the pedicle rod 1812 as a result of an eccentric axial force may then produce a transverse force in the force measurement apparatus that may then be measured by force sensor 1814.

Thus, a force concentrator consistent with the present disclosure may be utilized with a loadbearing medical device such as a pedicle screw system.

Figure 19:
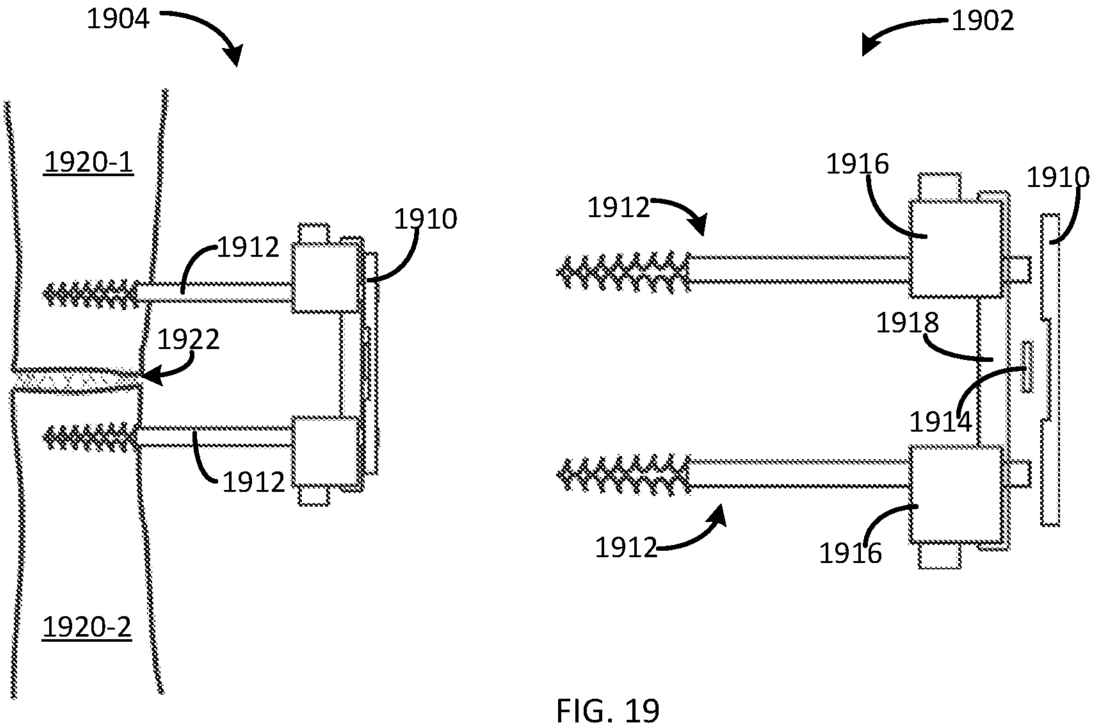
FIG. 19 illustrates an external fixator example application of a force measuring apparatus consistent with the present disclosure.

FIG. 19 illustrates an external fixator example application of a force measuring apparatus consistent with the present disclosure. In this example 1900, the force concentrator may be utilized in an external fixator system (an example of a loadbearing medical device) for fixing fractures. An external fixator system is similar to a fracture plate but a portion is configured to sit outside of the skin. Example 1900 includes a exploded side view 1902 of an external fixator system and an assembled side view 1904 of the external fixator system attached to a bone. Example 1900 includes a force concentrator 1910, a plurality of threaded pins 1912, a force sensor 1914, a plurality of clamps (i.e., connectors) 1916 and a rod (i.e., a bar) 1918. The assembled side view 1904 illustrates the assembled fixator system and force measuring apparatus attached to a fractured bone. The fractured bone has a first portion 1920-1 and a second portion 1920-2 separated by a gap 1922.

Force concentrator 1910 and the force sensor 1914 may be attached to the rod 1918. The rod 1918 may then be attached to the pins 1912 by the clamps 1916. Deflection of the rod 1918 as a result of an eccentric axial force may then produce a transverse force in the force measurement apparatus that may then be measured by force sensor 1914.

Thus, a force concentrator consistent with the present disclosure may be utilized with a loadbearing medical device such as an external fixator system.

Figure 20:
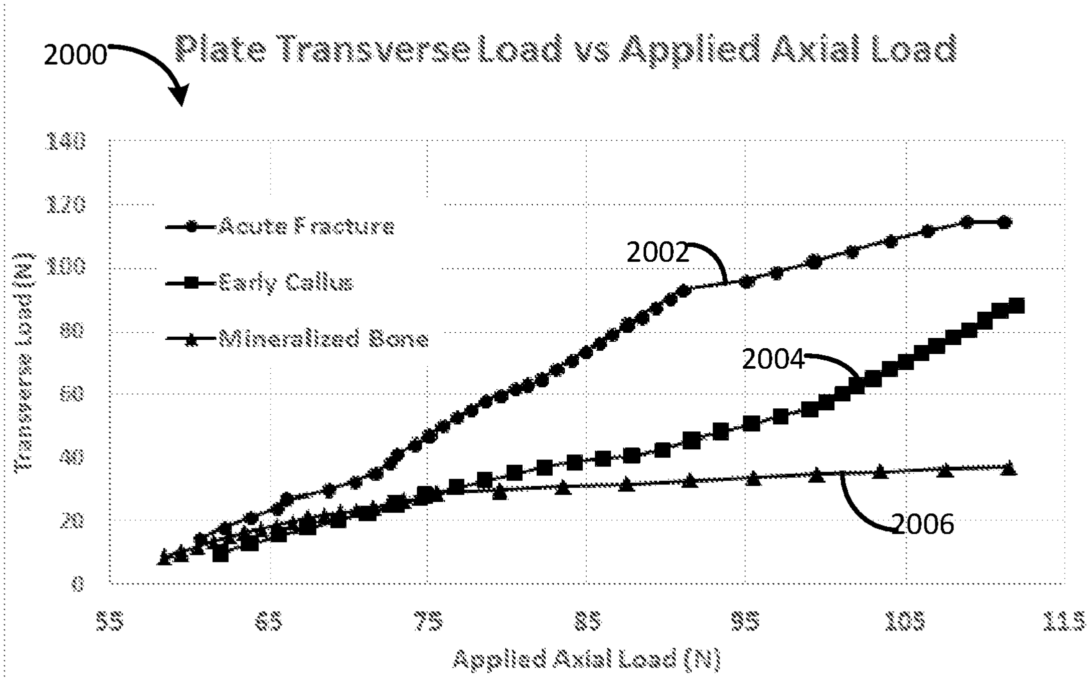
FIG. 20 is a plot illustrating experimental data for a test system utilizing a simulated fracture plate and a force sensing apparatus, consistent with one embodiment of the present disclosure.

FIG. 20 is a plot 2000 illustrating experimental data for a test system utilizing a simulated fracture plate and a force sensing apparatus, consistent with one embodiment of the present disclosure. In the test setup, two pieces of a simulated bone separated by a gap were used to simulate a fractured bone. An axial load was applied to the simulated bone and a transvers force between the fracture plate and the force concentrator was measured. In the plot 2000, a horizontal axis corresponds to applied axial load in units of Newtons (N) and a vertical axis corresponds to transverse load, in units of Newtons. An acute fracture curve 2002 corresponds to a simulation with the gap containing only air. An early callus curve 2004 corresponds to a simulation with the gap containing silicone, simulating early callus formation. A mineralized bone curve 2006 corresponds to a simulation with the gap containing a puck of a plastic material to simulate the mineralized bone.

Thus, a force measuring apparatus may include a force concentrator configured to attach to a loadbearing medical device. A bending stiffness of the force concentrator is different from a bending stiffness of the loadbearing medical device. When attached to the loadbearing medical device, the force concentrator is configured to produce a transverse force related to an eccentric axial force applied to the loadbearing medical device. The eccentric axial force is related to an axial force applied to the bone that is attached to the loadbearing medical device. The transverse force may then be measured by an axial force sensor attached to the loadbearing medical device, positioned transverse to the axial direction of the load and configured to measure a transverse force between the loadbearing medical device and the force concentrator.

What is claimed is:

1. An apparatus comprising:

a force concentrator attached to a loadbearing medical device, the force concentrator configured to span across a bone fracture when the loadbearing medical device spans across the bone fracture in a transverse direction such that a portion of the loadbearing medical device would be attached to a bone on one side of the bone fracture and a second portion of the loadbearing medical device would be attached to the bone on another side of the fracture, the force concentrator producing a transverse force between the force concentrator and the loadbearing medical device when an eccentric axial force is applied to the loadbearing medical device, wherein there is a difference in bending stiffness between the force concentrator and the loadbearing medical device, such that the bending stiffness of the force concentrator is less than the bending stiffness of the loadbearing medical device, wherein the difference in bending stiffness facilitates the production of the transverse force between the force concentrator and the loadbearing medical device.

2. The apparatus of claim 1, wherein the force concentrator defines at least one aperture configured to align with an aperture defined in the loadbearing medical device and configured to receive a fastener, the fastener configured to attach the force concentrator to the loadbearing medical device and to attach the loadbearing medical device to a bone structure.

3. The apparatus of claim 1, wherein the force concentrator comprises at least one attachment feature configured to engage with a corresponding attachment feature defined in the loadbearing medical device to attach the force concentrator to the loadbearing medical device.

4. The apparatus of claim 1, wherein the force concentrator has an inner surface, an opposing outer surface and a side surface coupled between the inner surface and the outer surface, a portion of the inner surface configured to contact an outer surface of the loadbearing medical device.

5. The apparatus of claim 1, wherein the force concentrator comprises at least one tensile member.

6. The apparatus of claim 1, wherein the force concentrator is constructed of a material selected from the group comprising metals, polymers and composite materials.

7. The apparatus of claim 1, wherein a shape of the force concentrator is determined based, at least in part, on a target bending stiffness of the force concentrator.

8. An apparatus comprising:

a force concentrator having two ends, attached at each of the two ends to a loadbearing medical device, the loadbearing medical device being a single piece plate, the force concentrator producing a transverse force between the force concentrator and the loadbearing medical device when an eccentric axial force is applied to the loadbearing medical device, wherein the loadbearing medical device is configured to span across a bone fracture such that a portion of the loadbearing medical device would be attached to the bone on one side of the bone fracture and a second portion of the loadbearing medical device would be attached to the bone on the other side of the fracture, wherein there is a difference in bending stiffness between the force concentrator and the loadbearing medical device, such that the bending stiffness of the force concentrator is less than the bending stiffness of the loadbearing medical device, wherein the difference in bending stiffness facilitates the production of the transverse force between the force concentrator and the loadbearing medical device.

* * * * *